(12) United States Patent
Jaffee et al.

(10) Patent No.: US 6,358,682 B1
(45) Date of Patent: Mar. 19, 2002

(54) METHOD AND KIT FOR THE PROGNOSTICATION OF BREAST CANCER

(75) Inventors: Deborah R. Jaffee, Laytonsville, MD (US); Kerry J. Flom, Highland Park, IL (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/237,115

(22) Filed: Jan. 26, 1999

Related U.S. Application Data

(60) Provisional application No. 60/072,574, filed on Jan. 26, 1998.

(51) Int. Cl.[7] .............................. C12Q 1/68; C12P 19/34
(52) U.S. Cl. ........................................... 435/6; 435/91.2
(58) Field of Search .................... 435/6, 91.2; 536/22.1

(56) References Cited

U.S. PATENT DOCUMENTS 4,968,603 A * 11/1990 Slamon et al. .................. 435/6

OTHER PUBLICATIONS

Iglehart et al (Cencer Research 50:6701–6707 1990.*

Vijver et al (New England J. Medicine 319:1239–1245 1988.*

* cited by examiner

*Primary Examiner*—Eggerton A. Campbell
(74) *Attorney, Agent, or Firm*—Heslin Rothenberg Farley & Mesiti P.C.

(57) ABSTRACT

This invention relates to a method, kit and controls for detecting HER-2/neu gene amplification as a predictor of breast cancer reoccurrence and patient survival The method is a fluorescent in-situ hybridization (FISH) assay using a labeled DNA probe. By determining the genetic nature of the cancer cells, appropriate treatment may be utilized. Control tumor cell lines with predefined amounts of HER-2/neu gene amplification are also disclosed.

16 Claims, 2 Drawing Sheets

SEQUENCE LISTING

<160> NUMBER OF SEQ ID NOS: 2

<210> SEQ ID NO 1
<211> LENGTH: 22

```
-continued

<212> TYPE: DNA
<213> ORGANISM: Artificial Sequence
<220> FEATURE:
<223> OTHER INFORMATION: Description of Artificial Sequence:PRIMER

<400> SEQUENCE: 1
cggccaagat ccgggagttg gt                                              22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 2
tcttgatgcc agcagaagtc aggc                                            24
```

METHOD AND KIT FOR THE PROGNOSTICATION OF BREAST CANCER

This application is a continuation-in-part of U.S. provisional patent application Serial No. 60/072,574, filed Jan. 26, 1998.

BACKGROUND OF THE INVENTION

1. Field of the Invention

The present invention relates to determining the prognosis of a patient with breast cancer by determining whether the HER-2/neu gene is amplified in tumor cells.

2. Description of Related Art

Breast cancer remains a major cause of illness and death among women in the United States, with over 180,000 new cases and 44,000 deaths per year (American Cancer Society, 1997). Possibly the most important predictor of clinical course in breast cancer is the presence or absence of lymph node metastases. Many prognostic indicators aid in evaluation of invasive cancers in addition to the presence or absence of lymph node metastasis, including tumor size, histologic type, tumor grade (differentiation reflected in extent of gland formation), nuclear grade (extent of nuclear alteration and frequency of mitosis), DNA content (ploidy), and hormone receptor status. A reasonable and desirable approach would be the use of prognostic factors to risk-stratify invasive breast cancer patients into low-risk and high-risk groups in terms of the probability of recurrence (McGuire, el al., 1990).

The HER-2/neu (ERBB2) gene is an oncogene which shares significant homology to the epidermal growth factor receptor (EGFR) gene (Yamamoto, et al, 1986) and the retroviral gene v-erbB. It was first detected as a mutated transforming gene in chemically induced rat neuronal tumors. It has been isolated from diverse sources, including: rat neuroblastoma (Schechter et al, 1985); human tumor lines from gastric cancer (Fukushige et al, 1986); salivary adenocarcinoma (Semba et al, 1985); and a human breast cancer cell line where HER-2/neu was identified in an amplified form (King et al, 1985). The gene has been localized to 17q11.2q12 (Human Gene Mapping 11, 1991), in a region where several genes relevant to breast cancer are located, including BRCA1 estradiol-17β dehydrogenase, NM23 and RARA.

Current evidence indicates that HER-2/neu protein over expression and gene amplification are indicative of poor patient prognosis at all stages of breast tumor development. Amplification appears early in tumor progression (Iglehart et al 1990 and Van de Vijver et al 1988), and when present is homogeneously distributed throughout the tumor (Press et al, 1994). Thus, it is a logical choice as a prognostic marker when used as an adjunct with other accepted prognostic indicators.

While such immunoassays for Her-2/neu protein have been commercially available, interpreting results is somewhat difficult. Protein denaturation or degradation during handling, staining embedding in paraffin and sectioning gives variable results, including both false negatives and false positives. Additionally, slightly different conditions during antibody-antigen binding results in false positives and false negatives. Unacceptable results have been reported for immunohistochemical detection of HER-2/neu amplification. See Thor et al 1989; Richner et al, 1990; O'Reilly et al, 1991; and Loveldn et al, 1991. By contrast counting the number of copies of the HER-2/neu gene in a cell represents a more objective determination and involves DNA markers which are less susceptible to degradation and provide less variable results.

HER-2/neu gene amplification status is useful as an adjunct in the evaluation of the prognosis of node negative breast cancer patients and is also an independent marker of high risk in node negative patients. Amplification of HER-2/neu is indicative of poor patient prognosis at all stages of breast cancer development and correlates with relatively shorter disease-free and overall survival.

Studies have shown positive correlation between HER-2/neu gene amplification and other common indicators of poor prognosis in breast cancer (Tsuda, et al, 1989 and Seshadri, et al., 1993 and Slamon et al, U.S. Pat. No. 4,968,603). However, even strong breast cancer prognostic factors, such as number of positive lymph nodes, tumor size and histograde do not predict patient outcome unfalteringly (Wright, et al., 1989 and Ro, et al., 1989). Current evidence indicates that HER-2/neu protein over expression and gene amplification are indicative of poor patient prognosis at all stages of breast cancer development (Seshadri, et al., 1993, Wright, et al., 1989 and Niehans et al., 1993). Because HER-2/neu amplification appears early in breast cancer progression (Iglehart, et al., 1990 and van de Vijver, et al., 1988) and, when present is homogeneously distributed throughout the cancer (Iglehart, et al., 1990 and Press, et al., 1994), it can serve as a prognostic marker for this disease (when used as an adjunct with other accepted prognostic indicators).

The use of Fluorescent In-Situ Hybridization (FISH) targeted to the HER-2/neu gene, has successfully demonstrated gene amplification in breast cancer cell lines and primary tumors, and has shown that FISH results are concordant with other measures of amplification (Kallioniemi, et al, 1992). [The gene has been localized to 17q11.2-q12 (Human Gene Mapping 11, 1991), in a region where several genes relevant to breast cancer are located, including BRCA1, estradiol-17 dehydrogenase, NM23, and RARA.] FISH technology combines the advantages of direct gene amplification assessment with direct localization in morphologically identified tumor cells. FISH is applicable to tumors of all sizes because studies can be performed on sections from the original specimen blocks used for diagnosis. In many samples, direct comparison can be made with FISH assays on normal cells from the same preparation. Further, if amplification were localized rather than diffusely distributed within a tumor, it would be detectable by FISH but could be diluted below detectable limits in extracted tumor DNA required for other procedures.

When performing an assay of such importance to the patient, it is critical to have appropriate controls. Sections of previously tested tissue are somewhat undesirable as controls due to cell variability, unclear boarders, necrotic tissue in the center of the tumor, variable responses to protease digestions and finite source material. Therefore, there is a need for quality control materials which can be run with every test which lack the above mentioned problems.

There is also a need for a set of statistical benchmarks to allow the medical practitioner to stratify the patient according to likelihood of cancer recurrence. This will aid the practitioner and patient in deciding whether aggressive treatments (e.g. chemotherapy, radiation and anti-HER-2/neu therapy) should be employed in lieu of a passive "watchful waiting" approach.

SUMMARY OF THE INVENTION

The present invention is directed to methods and reagents which determine the number of copies of the HER-2/neu gene in a breast cancer specimen. This method uses a FISH assay for HER-2/neu in surgically removed breast cancer tissue. Determination of an abnormally high copy number of the gene correlates with poor prognosis and such patients should be treated aggressively.

The present invention is also directed to a set of control slides, one of which has a normal copy number of the HER-2/neu gene, one has a high copy number of the HER-2/neu gene and one has a slightly elevated copy number of the HER-2/neu gene.

The present invention further includes the preparation of control slides using cell lines instead of primary tumor tissue. The preferred cell lines used for controls are one with high amplification of the HER-2/neu gene, one with non-amplification and one with low amplification.

The HER-2/neu gene detection system of the present invention is a kit consisting of DNA probe and detection reagents that yields a green fluorescent signal at the site of each HER-2/neu gene, on a blue fluorescent background of stained nuclear DNA The kit is intended to be used with sections (4 µm) of formal fixed, paraffin-embedded human breast cancer tissue. The kit is untended to include or recommend the use of another kit which includes the control lines.

The HER-2/neu gene detection system of the present invention is preferably a fluorescence in situ hybridization (FISH) DNA probe assay that determines the qualitative presence of HER-2/neu gene amplification on formalin-fixed, paraffin-embedded human breast tissue as an aid to stratify breast cancer patients according to risk for recurrence or disease-related death. It is indicated for use as an adjunct to existing clinical and pathologic information currently used as prognostic indicators in the risk stratification of breast cancer in patients who have had a primary, invasive, localized breast carcinoma and who are lymph node-negative.

A recent review and comparison is Ross et al, *The Oncologist* 3: 237–252 (1998).

DETAILED DESCRIPTION OF THE INVENTION

Figure 1:
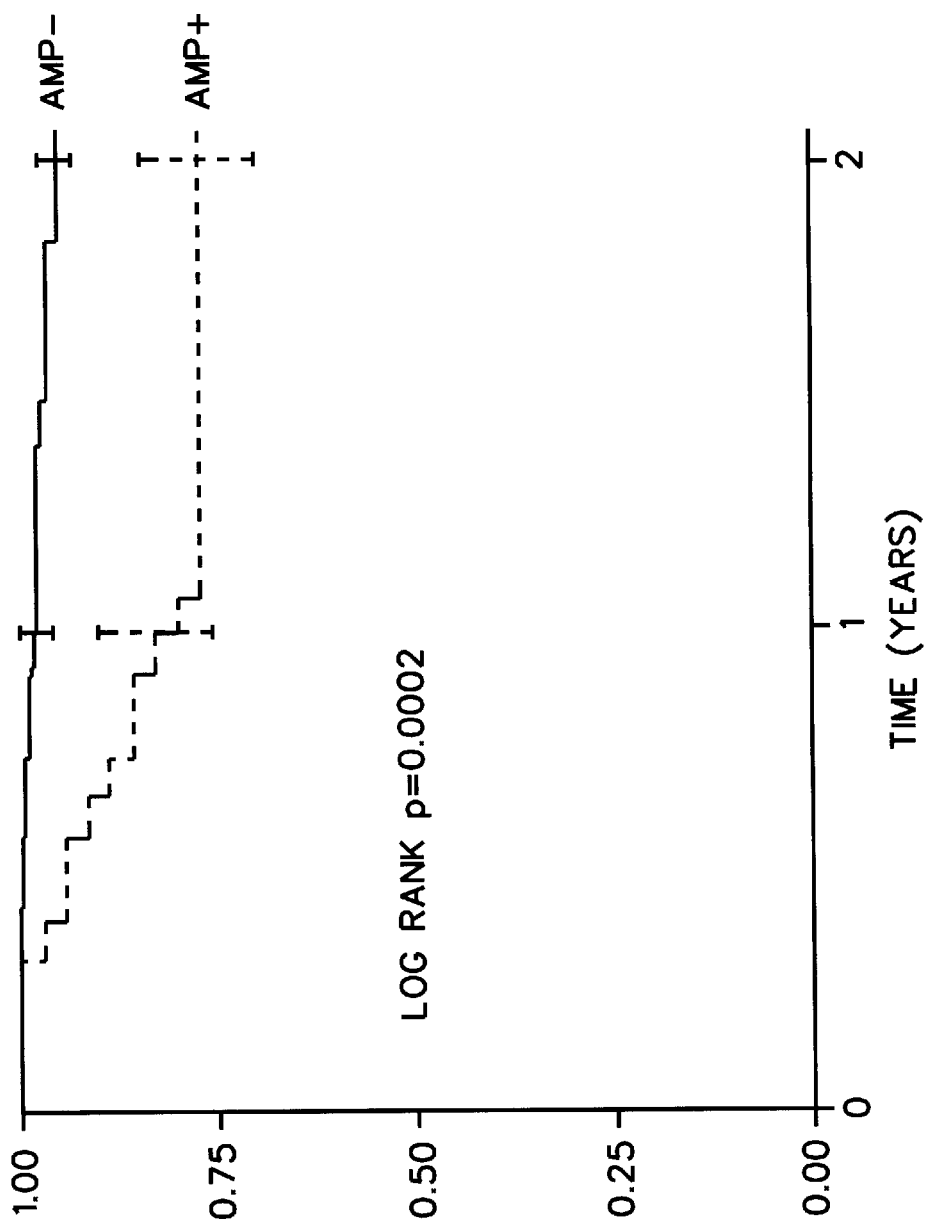
FIG. 1 is a survival curve of HER-2/neu amplification status with the cumulative probability of early recurrence.

The HER-2/neu gene amplification detection system according to the present invention is a fluorescence in situ hybridization (FISH) DNA probe assay intended for formalin fixed, paraffin-embedded human breast tissue as an aid in predicting risk of breast cancer recurrence so that patient management decisions can be improved. Post surgery lymph node negative patients with no amplification may receive little or no further treatment whereas patients with tumors having the HER-2/neu gene amplified may receive more aggressive monitoring, chemotherapy and/or radiation. Clearly, the appropriate use of the drug HERCEPTIN® (Genentech, South San Frisco, Calif.), humanized monoclonal antibody to HER-2/neu, is determinable by measuring HER-2/neu gene amplification. In the few months since release of the commercial assay it has become accepted standard practice to include the HER-2/neu gene amplification detection system routinely on breast cancer patients and particularly before the particular therapy noted above.

The relationship between HER-2/neu gene amplification and probability of remaining disease free and surviving is demonstrated in the Figures. These clinical studies are based on breast cancer patients who had excision of a primary, invasive, localized breast tumor, who were node negative and who did not receive any adjuvant therapy except in cases of disease recurrence. While remaining disease-free is somewhat different from survival, both measures are important even when the data does not exactly parallel.

While this specification is described with respect to breast cancer, one skilled in the art will readily appreciate the application of the techniques herein described of use with other cancers where the HER-2/neu gene is amplified, such as ovarian, prostate, endometrial and certain colon cancers. In such situations, different control cell lines and different amplification cut off numbers may be required but the need for appropriate quality controls remains.

Briefly, the methodology is as follows. Sections of formalin-fixed, paraffin-embedded breast cancer tissue mounted on microscope slides are pretreated chemically (Pretreatment Step, reduction of peptide disulfide bonds) and enzymatically (Protein Digestion Step, digestion of proteins) to remove proteins that block DNA access. The DNA in the sections is converted from double- to single-strand by solution denaturation at 75° C. using a mixture of 20×SSC (saline sodium citrate) and formamide. A hybridization solution, containing labeled DNA probe which is complementary to the HER-2/neu gene sequence, is applied to the tissue section, which is then incubated under conditions favorable for annealing of probe DNA and genomic DNA sequences. Unannealed probe is washed off using a mixture of 20×SSC and formamide. The hybridized probe is detected using a fluorescently-tagged ligand (fluorescein-labeled avidin) which binds to the label on the DNA probe, thereby immobilizing the fluorescein at the site of the HER-2/neu gene. The remainder of the DNA is then stained with an intercalating fluorescent counterstin DAPI in Antifade). Excitement of fluorescein and DAPI by light from a mercury arc lamp with appropriate filters in an epifluorescence microscope results in the emission of green and blue light, respectively. The observer selects for these two colors by using a microscope filter set designed for simultaneous viewing of DAPI and fluorescein, and scores nuclei in the tissue section for the number of green signals on a blue background.

When performing such an assay of great importance to the patient, it is always necessary to use the best available controls. Tissue sections from an excised tumor are somewhat variable by being a mixed population of cells, sometimes having unclear boarders. Tissue sections can only be as good at the tumor itself which may have a necrotic center, have blood vessels through it, and contain a number of inflammatory response cells. The density of cells in a primary tissue section (tumor or normal) may be high with a 4 µm thick section having only a small part of a cell. In FISH assays, a protein digestion step is performed. The digestion conditions differ between different tumors and normal cell types. All of this requires skilled individuals to determine which cells are appropriate tumor cells to be considered on the slide. Additionally, tumor and normal sections represent a finite source of controls as each new tissue block will require rest and ardization before it can become a control standard.

By comparison, cell lines have the advantage of uniformity in cell type with no chance of misidentifying the cells.

The cell concentration is regulatable so that the control slide will have cells evenly distributed and clearly separated. Since the cell line is uniform, the protein digestion conditions may be perfected, not merely optimized. Uniformity also reduces interpretation mistakes and permits use of less skilled, and less expensive, personnel. Because cell lines are used, the exact cell type may be used indefinitely as an permanent source of control cells without further need to restandardize the cell line. Should doubt remain as to the advantages of standardized controls over previously tested samples, several subclasses of U.S. patents are devoted to analytical clinical controls, their preparation and use.

In the present invention, the control slides include a slide with a normal copy number of the HER-2/neu gene, a slide with a highly amplified copy number of the HER-2/neu gene, and a slide with a lowly amplified copy number of the HER-2/neu gene. Representative examples are:

| Level 1 Control ATCC HTB 132 (MDA-MB-468) | non-amplification, $\leq 3$ copies per cell |
|---|---|
| Level 2 Control ATCC HTB 133 (T-47D) | low amplification, 3–10 copies per cell |
| Level 3 Control ATCC HTB 30 (SK-BR-3) | high amplification, $\geq 10$ copies per cell |

The use of a control with a low level of amplification is preferred as clinical samples with low levels of gene amplification are the mostly likely to be miss detected. Such primary cancers may be difficult to find and standardize, thus the use of such a cell line has considerable benefits.

It will be appreciated that numerous other cell lines may be used as controls provided that the number of copies of HER-2/neu gene is adequately quantified and it is uniform in the cell line. Cell line controls should fall into one of the three level control ranges recited above. Once another cell line has been so standardized, it may be used in lieu of the specific cell lines recited above. It is preferred to use tumor cell lines originating from the same tissue as being tested from the patient. For example, the three cell lines above originated from breast cancers.

Briefly, control slides are prepared by culturing the cell lines, suspending a predetermined concentration of cells in plasma, clotting the plasma, formalin fixing, embedding in paraffin, sectioning and mounting on a slide. It should be noted that additional and alternative steps of preparing the slide for FISH may also be performed with a goal of preparing the control cell line to resemble breast tumor tissue for comparative parallel testing. Such sample preparation techniques are described for example, in *Diaiostic Molecular Pathology*, Vol. 1, IRL Press, N,Y.

While these steps are individually well known in the art, numerous variations on the above procedure may be used. For example, other solidifying materials may be used in the place of plasma provided that they do not alter the cellular DNA. Examples include agarose, gelatin, pectin, alginate, carrageenan, monomers, polymers etc. where the gel is formed by cooling, adding ions (calcium, potassium) adding a polymerizing or a cross linking agent, etc. Other fixatives are known and may be used if any is desired at all. Paraffin embedding may be standard but other similar materials may be used and may even be optional. Likewise, the thickness of the section cut from a block is variable and is optimized depending on the microscope and assay conditions.

The relative sensitivity and specificity of the HER-2/neu gene amplification detection system for measuring HER-2/neu gene copy numbers was accessed. Breast cancer specimens with a known HER-2/neu gene copy and expression levels were selected as archival tissue specimens. Amplification was previously determined by Southern Blot hybridization or dot blot using extracted DNA. Expression had been determined by Northern hybridization, Western immunoblotting and/or immunohistochemistry using total RNA, total protein or histologic sections from tumor tissue. Slamon et al, 1989 and Press et al, 1993. Gene amplification levels correlated with gene expression levels in approximately 90% of the breast cancers under research conditions. In a less standardized clinical setting, the divergence may be higher. The comparison with FISH was performed by the HER-2/neu gene amplification gene detection system on 140 breast cancer specimens. Forty-nine were considered true positive, 90 true negative, 0 false positive and 1 false negative. This is a the relative sensitivity value of 98% and the relatively specificity value of 100%.

The expected HER-2/neu gene detection system assay result in normal breast tissue (non-cancerous) was estimated in a population of 20 breast tissue samples from reduction mammoplasties. The overall observed mean was 2.2 signals per nucleus with a range of 1.8–2.6 signals per nucleus. The target population for analysis using the HER-2/neu gene detection system was patients with primary node-negative, invasive breast carcinoma. The expected prevalence of early recurrence within 2 years is 4 to 6%. The expected prevalence of recurrence within 3 years is 2 to 10%. The expected prevalence of disease related death (within 3 years) is 10 to 15% (Clinical Oncology, 1993, page 207).

A clinical study evaluated HER-2/neu gene amplification status in 220 women with node negative invasive breast cancer whose only course of treatment was surgery, unless diagnosed with disease recurrence. For this study population HER-2/neu amplification was shown to have predictive power independent of the other prognostic markers evaluated (patient age at diagnosis, tumor size, tumor grade, and estrogen receptor). HER-2/neu was shown to be the strongest predictor for early recurrence (within 24 months), recurrence and disease-related death.

The negative predictive value, probability of no disease being present in women with HER-2/neu non amplified tumors, was found to be high three years after diagnosis (93.3% based on a prevalence of 10.4%). The probability of being alive three years after diagnosis was 99.4%, based on a prevalence of 2.4%.

HER-2/neu was analyzed along with and controlling for the above listed prognostic factors. The combined effect (interaction) of tumor size and HER-2/neu amplification status is presented in FIG. 2. One analysis used tumor size at 1 cm and additional analysis looked at tumor size at 2 cm. In both sets of analyses, tumor size is not significant (p>0.05) for predicting recurrence and disease-related death when the tumor is HER-2/neu amplified.

When the tumor is not amplified for the HER-2/neu gene, tumor size is also an insignificant predictor of recurrence and disease-related death within 3 years. With longer follow-up, disease-related death was significantly predicted in a comparison of tumors>1 cm. In this particular data set, there were no disease-related deaths for HER-2/neu non-amplified tumors.

These data show that for this study tumor size failed to be a good predictor of recurrence and disease-related death within 3 years. Tumor size is of little consequence in HER-2/neu positive tumors and orny becomes of value when evaluating disease-related death, in HER-2/neu negative tumors. HER-2/neu amplification was shown to have predictive power independent of all other prognostic markers evaluated and to be the strongest predictor for recurrence and disease-related death.

The following Examples utilized the commercially available Oncor INFORM HER-2/neu Gene Detection System (Ventana Medical Systems, Gaithersburg, Md., USA), Cat. No: S8000-KIT. The Procedure and Interpretation Guide enclosed with the kit is expressly incorporated by reference. This kit was the subject of a FDA PMA No. P9400004, the public contents of which are expressly incorporated by reference.

EXAMPLE I

PREPARATION OF HER-2/neu PROBES

Partial restriction enzyme digests of human Chromosome 17 DNA were prepared to create a library. Fragments were cloned into BAM HI restriction sites on a cosmid vector and grown in E. Coli HB 101. Positive clones were selected with Kanamycin containing medium. The cosmid probe set represent overlapping segments with a four member contig. A probe used to detect the cDNA is preparable using primers 5'-CGGCCAAGATCCGGGAGTTGGT-3' SEQ ID NO: 1 and 5'-TCTTGATGCCAGCAGAAGTCAGGC-3' SEQ ID NO: 2. Numerous publications exist regarding the HER-2/neu gene and other probes may be prepared and used.

Biotintylated HER-2/neu DNA probe was prepared containing a biotin-labeled single-stranded DNA fragment derived from human genomic DNA sequences, suspended in a solution of formamide, SSC and blocking DNA The probe DNA sequences are complementary to the sample HER-2/neu (erb-b2) gene sequence and specifically bind to them upon hybridization. The probe used below is the commercially available HER-2/neu probe (Ventana Medical Systems, Gaithersburg, Md.)

EXAMPLE II

SAMPLE PREPARATION FOR FISH ASSAY FOR HER-2/neu

Slides were prepared by cutting paraffin embedded tissue samples into 4 $\mu$m thin sections and applying them to silanized or positively charged slides. The slides were air dried and baked at 65° C.±5° C. overnight. The slides were deparaffinized in fresh xylene that has not been used for more than one week and repeated through three changes of xylene for five minutes each. The slides were then washed in fresh 100% ethanol that has not been used for more than one week for two minutes. The ethanol washing was repeated and the slides allowed to air dry.

The slides were pretreated by immersing slides in a coplin jar containing 40 ml of pre-warmed 30% w/v sodium bisulfite Pretreatment Solution in a 43° C.±2° C. water bath for 15 minutes. This solution is designed to reduce disulfide bonds, aid in protein digestion and improve probe penetration to target DNA sequences. The slides were then washed in 40 ml of 2xSSC at room temperature for 1 minute and then washed twice using fresh 2xSSC. The slides were then dehydrated through a room-temperature graded series of ethanol solutions for 2 minutes in each of 70%, 80%, 90%o and 100% ethanol and allowed to air dry inclined with label end down.

40 ml of Protein Digesting Enzyme Working Solution was freshly prepared by mixing 25 mg of proteinase K in 37° C.±2° C. of prewarmed 2xSSC. Slides were immersed in a coplin jar of prewarmed Protein Digesting Enzyme Working Solution and incubated at 37° C.±2° C. for 40 minutes. This solution is needed to digest protein and improve probe penetration. The slides were washed three times in 40 ml of fresh 2xSSC at room temperature for 1 minute. The slides were dehydrated through the room-temperature graded series of ethanol solutions for 2 minutes in each grade of ethanol: 70%, 80%, 900% and 100% and allowed to air dry inclined with label end down.

The slides were denatured by immersing them in a coplin jar containing 40 ml of pre-warmed Denaturation Solution (70% formamide/2xSSC, pH 7.0) in a 75° C. water bath for 8 minutes. The slides were immediately transferred to the pre-chilled (−20° C.±5° C.) 70% ethanol and rinsed for 2 minutes. The rinse was repeated in pre-chilled (−20° C.±5° C.) 80%, 90%, and 100% ethanol solutions, successively and allowed to air dry inclined with label end down.

The HER-2/neu DNA probe was prewarmed at 37° C.±2° C. for 5 minutes, vortexed for 1 minute and centrifuged for 2 to 3 seconds to collect contents in the bottom of the tube. 10 $\mu$l of probe solution was pipetted onto the denatured tissue section and covered gently with a 25 mm×25 mm glass coverslip. Larger tissue sections may require up to 20 $\mu$l of probe and larger glass coverslips. The slides were incubated at 37° C.±2° C. for 12 to 16 hours in a humidified chamber.

The coverslips were then removed by sliding it to the side and lifting the overhanging edge with forceps. The slides were washed in a coplin jar containing 40 ml of pre-warmed Post-Hybridization Wash Solution (50% Formamide/2x SSC, pH 7.0) in the 43° C.±° C. water bath for 15 minutes. The slides were then rinsed in a coplin jar containing 40 ml of pre-warmed 2xSSC in the 37° C. water bath with frequent agitation for 10 minutes and repeated with fresh 2xSSC and placed in a coplin jar containing 40 ml of 1xPBD (phosphate buffered detergent) at 18° C. to 25° C.

60 $\mu$l of Blocking Reagent One (0.05 g nonfat dry milk, Nonidet P-40, phosphate buffer and sodium azide) was added to each slide, a plastic coverslip placed over the solution and incubated 5 minutes in a humidified chamber at room temperature. The plastic coverslip was pealed off and blotted dry for re-use. The slide was tilted to allow fluid to drain briefly. This reagent contains salts, detergent, proteins and sodium azide (preservative) which aid in reducing non-specific binding of fluorescein-labeled avidin to the hybridized and washed tissue section.

60 $\mu$l of Detection Reagent (fluorescein labeled avidin in sodium azide preservative) was added to each slide and the plastic coverslip replaced over the solution. The slide was incubated 20 minutes in a humidified chamber at room temperature. After 10 minutes of the 20 minute incubation, one lifts and replaces the plastic coverslip to ensure even fluid distribution. This reagent detects hybridized probe DNA by binding to the biotin conjugated to the probe.

The plastic coverslip was then pealed off and discarded. The slides were washed in a coplin jar containing 40 ml of 1xPBD at room temperature for 2 minutes and the wash repeated 2 times using fresh 1xPBD.

The slides were removed from 1xPBD, tilted to allow fluid to drain briefly, then excess fluid was briefly blotted from the edge.

60 $\mu$l of Blocking Reagent Two (0.05 ml goat serum, Nonidet P-40, phosphate buffer and sodium azide) was added to each slide and a fresh plastic coverslip placed over the solution. The slides were incubated 5 minutes in a humidified chamber at room temperature, the plastic coverslip pealed off and blotted dry for reuse and the slide tilted to allow fluid to drain briefly. This reagent is a mixture of salts, detergent and proteins in a sodium azide preservative which reduce non-specific binding of the Anti-Avidin Antibody to the hybridized ans washed tissue section during the signal amplification phase of detection.

60 µl of Biotin-labeled Anti-Avidin Antibody was added to each slide and the plastic coverslip replaced over the solution. Incubation was for 20 minutes in a humidified chamber at room temperature. At 10 minutes of incubation, the plastic coverslip was lifted and replaced to ensure even fluid distribution. This reagent binds to fluorescein-labeled avidin what has previously bound to the hybridized probe and allows amplification of the fluorescent signal by providing multiple additional biotin moieties for binding by fluorescein-labeled avidin for each one originally bound with probe. The reagent contains sodium azide as a preservative.

The plastic coverslip was removed and discarded. Slides were washed in a coplin jar containing 40 ml of 1xPBD at room temperature for 2 minutes. This wash was repeated 2 times using fresh 1xPBD.

60 µl of Blocking Reagent One was applied to each slide and a fresh plastic coverslip placed over the solution. Incubation was for 5 minutes in a humidified chamber at room temperature. After that the plastic coverslip was pealed and blotted dry for reuse while the slide was tilted to allow fluid to drain briefly.

60 µl of Detection Reagent was applied to each slide and the plastic coverslip replaced over the solution. Incubation was for 20 minutes in a humidified chamber at room temperature. After 10 minutes of incubation, the plastic coverslip was lifted and replaced to ensure even fluid distribution.

The plastic coverslip was pealed and discarded and the slides washed in a coplin jar containing 40 ml of 1xPBD at room temperature for 2 minutes. The wash was repeated 2 times using fresh 1xPBD.

The cell nuclei were counterstained by adding 20 µl of DAPI/Antifade (DAPI, glycerol, P-phenylene diamine dihydrochloride, sodium bicarbonate, sodium hydroxide in phosphate buffered saline) to each slide and covered with a 24x50 mm glass coverslip. Stained slides may be stored in the dark at −15° C. to −25° C. for up to five days before analysis. This reagent is a mixture of a blue-fluorescing DNA-intercalating dye and a chemical which reduces photo bleaching. This is used to counterstain nuclear DNA blue to prolong probe signal fluorescence.

If the tissue section was insufficiently digested under the designated digestion conditions and is determined to interfere with interpretation of assay results, an extended protein digestion may be used as follows. The coverslip was removed by gently wiping off the immersion oil with tissue paper and soaking the slide in 40 ml 2xSSC, pH 7.0 in a coplin jar at room temperature until the coverslip falls off The slide was placed in a coplin jar containing fresh 2xSSC, pH 7.0 for several minutes to clean off any residual DAPI/ Antifade.

The slides were placed in prewarmed Protein Digestion Enzyme Working Solution at 37° C.±2° C. The effect of this protein digestion and the initial digestion is cumulative. Twenty (20) additional minutes of digestion might be an appropriate starting time for tissue that seems very under-digested after the initial 40 minute digestion.

The slides were washed in 40 ml 2xSSC, pH 7.0 room temperature with agitation for 10 seconds, then dehydrated in 70%, 80%, 90%, and 100% ethanol at room temperature for 1 minute each and allowed to air dry. The process above is then repeated.

EXAMPLE III

PREPARATION OF CONTROL SLIDES

The control slides are prepared using the following cell lines:

| | |
|---|---|
| Level 1 Control | ATCC HTB 132 (MDA-MB-468) cell line |
| Level 2 Control | ATCC HTB 133 (T-47D) cell line |
| Level 3 Control | ATCC HTB 30 (SK-BR-3) cell line |

Each cell line is available from the American Type Culture Collection, Manassas, Va., USA and grown using standard media and techniques to produce approximately $1.5 \times 10^8$ cells. The cell growth is divided into approximately 30 $5 \times 10^6$ cells. Pellets of the cultured cells were suspended in a plasma/thrombin matrix and clotted. Fibrin clotted blocks were then formalin fixed. Each block is paraflin embedded, cut into 4 µm sections and mounted on a silanized glass slide. The HER-2/neu Control Slides were stored at 18° C. to 25° C. prior to processing and at −15° C. to −25° C. after processing

EXAMPLE IV

SCORING OF CONTROL SLIDES

A non-amplified sample has a mean HER-2/neu signal per nucleus less than or equal to ($\leq$) 4. Specimens with a mean signal per nucleus greater than (>) 4 are amplified for the HER-2/neu gene. Control Slides are divided into three (3) categories. These are listed below and should not be confused with the amplification cut-off value of 4.

LEVEL 1(0 to 3 signals/nucleus) CONTROL SLIDES

A Level 1 control has a mean signal per nucleus value of less than or equal to 3. This range of assay scores (0 to 3) is defined as non-amplified for the HER-2/neu gene. In most patient specimens, an internal non-amplified control is present in the form of cells that are identifiably non-cancerous by the criteria of histopathologic morphology.

Level 1 control slides are 4 µm sections of a formalin-fixed, paraffin-embedded human breast cancer tissue culture cell fine on silaized slides. The preferred cell line is MDA-MB468 (ATCC#HTB 132).

LEVEL 2 (>3 to <10 signals/nucleus) CONTROL SLIDES

A Level 2 control has a mean signal per nucleus value of greater than 3 to less than 10. This range of assay scores (>3 to <10) is defined as low amplified HER-2/neu gene amplification. Level 2 control slides are 4 µm sections of a fonnalin-fixed, paraffin-embedded human breast cancer tissue culture cell line on silanized slides. The preferred cell line is T471D (ATCC#HTB 133).

LEVEL 3 (SYMBOL≧210 signalsnmucleus) CONTROL SLIDES

Level 3 control specimens represent a highly amplified specimen. A Level 3 control has a mean signal per nucleus value equal to or greater than 10. This range of assay scores ($\geq 10$) is well above the cutoff of>4 signals per nucleus. Level 3 control slides are 4 µm sections of a formalin fixed, paraffin-embedded human breast cancer tissue culture cell line on silanized slides. The preferred cell line is SK-BR-3 (ATCC#HTB 30).

Level 1, Level 2 and Level 3 controls should be run and evaluated with each run of the HER-2/neu gene detection system assay. Paraffin-embedded human breast cancer cell lines are run simultaneously with each run of samples. The control slides are read by scoring 20 cells from each of two (2) randomly selected areas of the slide (total of 40 nuclei) and the results interpreted as described below. Scoring criteria for invasive cancer do not apply to the paraffin-embedded cell line controls.

Because breast cancer cell nuclei are often considerably thicker than the 4 μm sections of tissue required to perform the assay, the control tissue nuclei are frequently not intact. This effect of sectioning will result in the observation of fewer HER-2/neu signals than are actually contained in an intact nucleus.

The mean signal per nucleus of a Level 1 control must be less than the mean signal per nucleus of a Level 2 control for a processing run to be considered valid. For cell line controls acceptance ranges see the list below:

Based on 393 observations (40 nuclei scored per observation) of 4 μm sections of the Level 1 control cell line a mean of 2.4 (standard deviation=0.25) HER-2/neu signals per nucleus was determined.

Based on 102 observations (40 nuclei scored per observation) of 4 μm sections of the Level 2 control cell line, a mean of 3.5 (standard deviation=0.71) HER-2/neu signals per nucleus was determined.

Based on 338 observations (40 nuclei scored per observation) of 4 μm sections of the recommended Level 3 control cell line, an acceptance range of 15.8 to 20.0 HER-2/neu signals per nucleus was determined (determined by non-parametric analysis).

In addition to these HER-2/neu Control Slides, controls may also take the form of 4 μm tissue sections from invasive breast cancers that have been previously identified to have specific levels of HER-2/neu gene amplification by fluorescence in situ hybridization (FISH). Use of breast cancer tissue as control material requires qualification and validation by the user laboratory according to the laboratory's established procedures. While these controls may be useful to at or group tissues according to HER-2/neu amplification status such controls are time consuming to prepare and generally considered inferior to standardized controls. Additionally, controls from cell lines are homogeneous and reproducible, neither quality can be attributed to surgically removed tumors and their sections For determination of HER-2/nem gene amplification level in tissue specimens, 40 nuclei were scored from specimens processed with two (2) lots of the control cell lines. Multiple observers were used (3 or 4) to achieve accurate estiates of the mean and standard deviation (SD). Acceptance ranges were calculated from the mean plus and minus three (3) standard deviations. The results of six (6) Level 1 tissue specimens are summarized below.

TABLE 1

Examples of Level 1 Tissue Specimen Means and Acceptance Ranges

| Specimen | Mean ± SD, (no. of observations) | Acceptance Range |
|---|---|---|
| 1. | 1.96 ± 0.37, (N = 42) | 0.85–3.07 |
| 2 | 2.14 ± 0.79, (N = 42) | 0–4.51 |
| 3 | 2.01 ± 0.41, (N = 42) | 0.78–3.24 |
| 4 | 2.08 ± 0.64, (N = 42) | 0.16–4.00 |
| 5 | 1.70 ± 0.31, (N = 36) | 0.77–2.63 |
| 6 | 2.01 ± 0.29, (N = 36) | 1.14–2.88 |

In general, a 4 μm section of a Level 2 control tissue will exhibit a mean of greater than 3 to less than 10 (>3 to <10) HER-2/neu signals per nucleus (40 nuclei scored) when assayed with the HER-2/neu gene detection system of the present invention.

For determination of HER-2/neu gene amplification level in tissue specimens, 40 nuclei were scored from specimens processed with two (2) lots of the control slides, Multiple observers were used (3 or 4) to achieve accurate estimates of the mean and standard deviation (SD). Acceptance ranges were calculated from the mean plus and minus two (2) standard deviations. The results often (10) Level 2 tissue specimens are summarizd below.

TABLE 2

Examples of Level 2 Tissue Specimen Means and Acceptance Ranges

| Specimen | Mean ± SD, (no. of observations) | Acceptance Range |
|---|---|---|
| 1 | 3.93 ± 0.74, (N = 36) | 2.46–5.41 |
| 2 | 5.69 ± 1.31, (N = 36) | 3.07–8.31 |
| 3 | 3.97 ± 1.65, (N = 36) | 0.67–7.27 |
| 4 | 3.56 ± 0.47, (N = 36) | 2.62–4.50 |
| 5 | 3.05 ± 0.41, (N = 36) | 2.23–3.87 |
| 6 | 6.35 ± 1.06, (N = 51) | 4.23–8.47 |
| 7 | 8.07 ± 2.08, (N = 53) | 3.91–12.23 |
| 8 | 6.17 ± 2.19, (N = 36) | 1.79–10.55 |
| 9 | 5.52 ± 1.6, (N = 36) | 2.32–5.52 |
| 10 | 8.21 ± 2.47, (N = 30) | 3.27–13.51 |

In general, a 4 μm section of a Level 3 control tissue will exhibit a mean of greater than or equal to 10 HER-2/neu signals per nucleus (40 nuclei scored) when assayed with the HER-2/neu gene detection system.

In a study for determination of HER-2/neu gene amplification level in tissue specimens, 40 nuclei were scored from specimens processed with two (2) lots of the control slides. Multiple observers were used (3 or 4) to achieve accurate estimates of the mean. Acceptance ranges were calculated from the mean plus and minus two (2) standard deviations with the upper limit truncated at 20. The results of eight (8) Level 3 tissue specimens are summarized below.

TABLE 3

Examples of Level 3 Tissue Specimen Means and Acceptance Ranges

| Specimen | Mean (no. of observations) | Acceptance Range |
|---|---|---|
| 1 | 17.72 (N = 36) | 12.34–17.72 |
| 2 | 17.46 (N = 36) | 11.66–20.00* |
| 3 | 15.95 (N = 36) | 11.15–20.00 |
| 4 | 10.85 (N = 44) | 6.25–15.45 |
| 5 | 14.54 (N = 42) | 8.84–20.00 |
| 6 | 10.73 (N = 42) | 6.16–15.31 |
| 7 | 15.09 (N = 36) | 6.19–20.00 |
| 8 | 12.20 (N = 36) | 4.46–19.94 |

*Acceptance ranges >20 have been set to 20 as discussed in the Interpretation Section of this Procedure and Interpretation Guide.

EXAMPLE V

FISH ASSAY FOR HER-2/neu AMPLIFICATION ON CLINICAL SAMPLES

Slides were viewed with an epifluorescence microscope equipped with a DAPI filter set and a DAPI/FITC/Texas Red triple band pass filter set (a filter set capable of simultaneously passing FITC and DAPI fluorescence). A FITC/Texas Red dual band pass filter set (a filter set that allows visualization of the FITC signal but not the DAPI counterstain) is helpful in resoling background from true signal. The microscope may be equipped with 10×, 40× (optional for viewing hematoxylin and eosin stained sections) and 100× objectives and a 100 watt mercury arc light source. Scoring should be performed in a darkened room with excessive light leaking from microscopes minimized.

Using the DAPI filter set and the same low power objective used to view hematoxylin and eosin stained sections, it was confirmed that the tissue section contains areas of invasion as previously identified in hematoxylin and eosin stained sections. Areas of invasion are scored; carcinoma in situ should not be scored.

Using the DAPI/FITC/Texas Red triple band pass filter set and a 100× oil objective, the FITC signal was present in approximately ¾ or more of the cancer cell nuclei in the area to be scored.

It should be noted that non-cancerous cell nuclei (e.g. from normal epithelium) may be more resistant to protein digestion and may show lower levels of hybridization than tumor cell nuclei; therefore, these non-cancerous cell nuclei are not a reliable gauge of hybridization efficiency for the cancerous cell nuclei. The hybridization signals to be scored within a cancer cell nucleus will be of similar size and intensity, whether separated or clustered.

With the DAPI filter set and a 100× oil objective, individual cancer nuclei were selected for scoring. Only cancer nuclei that are non-overlapping are selected. Severely truncated cancer nuclei were excluded. Cancer nuclei that are less than ⅓ the diameter of the average cancer cell nucleus are not selected. Overdigested and mechanically damaged cancer cell nuclei are not selected. Only cancer cell nuclei that have relatively well-defined borders are selected to be scored.

Using the DAPI/FITC/rexas Red triple band pass filter set and a 100× oil objective, probe signals were differentiated from background if present. FITC stain appearing over cytoplasm or in the extra-cellular matrix is considered background. Background confined to the cancer nucleus is more difficult to interpret and could interfere with counting, but the background is generally much smaller and more diffuse than true probe signal.

Using the DAPI/FITC/Texas Red triple band pass filter set and a 100× oil objective, the number of FITC signals present in each of 20 randomly-selected cancer nuclei that meet all the above mentioned criteria were counted. In FISH analysis, signals are often in different planes of focus within the tumor cell nucleus. Focusing up and down through the section to find all of the signals present in the cancer cell nucleus was used. If the signal count is greater than 20 per cancer cell nucleus, it was recorded as 20+ and not grouped with any other counts.

Scoring in a second area of invasive breast cancer was repeated following all steps above. The two areas examined were separate, distinct microscopic areas within a single section. The total number of cancer nuclei scored was 40 from 2 distinct areas of the same lesion in one section the mean number of HER-2/neu signals per nucleus was determined.

If more than 5% of the fluorescein signals (those of similar size and intensity to true signal within invasive tumor nuclei) are located over the cytoplasmic compartment or extra cellular matrix and all troubleshooting methods have been exhausted, the background is excessive and the assay repeated.

When the positive or negative control results fall outside the expected values, then the specimen results are unreliable and the assay repeated.

When 40 non-overlapping nuclei cannot be identified, then the sample is inadequate and the assay repeated on a new slide.

When signal intensity varies widely after all troubleshooting methods have been exhausted, then the specimen results is unreliable and the assay repeated.

Values at or near the cut-off (3.5 to 4.5 mean signals/nucleus) are expected to occur in approximately 3.6% of the patient population. Scoring of borderline specimens should be repeated by another qualified user or the test should be repeated using a new tissue section. If the value of 3.5 to 4.5 persists, then the borderline results should be interpreted with caution and increased emphasis should be given to the other clinical and prognostic information available to the practitioner.

A retrospective study of 220 node-negative breast cancer patient specimens were collected from multiple sources and analyzed at two clinical sites in the United States. This combined data set was used to determine the association of HER-2/neu gene amplification, using the HER-2/neu gene detection system of the present invention, to the clinical outcomes; early recurrence (within 24 month of diagnosis), recurrences, and death, due to breast cancer.

The clinical performance characteristics of the HER-2/neu gene detection system are described with amplification defined as>4 signals per nucleus and non-amplification defined as<4 signals per nucleus.

The HER-2/neu gene detection system was used to retrospectively identify the risk of recurrence and death for node-negative breast cancer patients meeting the following criteria:

1) Diagnosis of invasive breast cancer,
2) Available formalin-fixed, paraffin-embedded tissue for HER-2/neu analysis;
3) Primary treatment surgery only;
4) Clinical follow up for at least 2 years for early recurrence, 3 years for recurrence and death.

The safety and effectiveness of the HER-2/neu Gene Detection System was evaluated in a population of 220 node-negative, invasive breast cancer patients for early recurrence within two years. Two hundred twelve (212) of the 220 specimens were eligible for evaluation of recurrence at anytime and 210 of the 220 specimens were eligible for evaluation of disease-related death. (Eight (8) subjects did not recur and were lost to follow-up before 36 months; ten (10) subjects did not die of their disease and were lost to follow-up before 36 months.) The relationship of the HER-2/neu gene detection system assay result to the probability of remaining recurrence-free (disease-free survival) in lymph node negative breast cancer is presented in Table 4. The relationship of the assay results to the probability of surviving (overall survival) is shown in Table 5.

Figure 2:
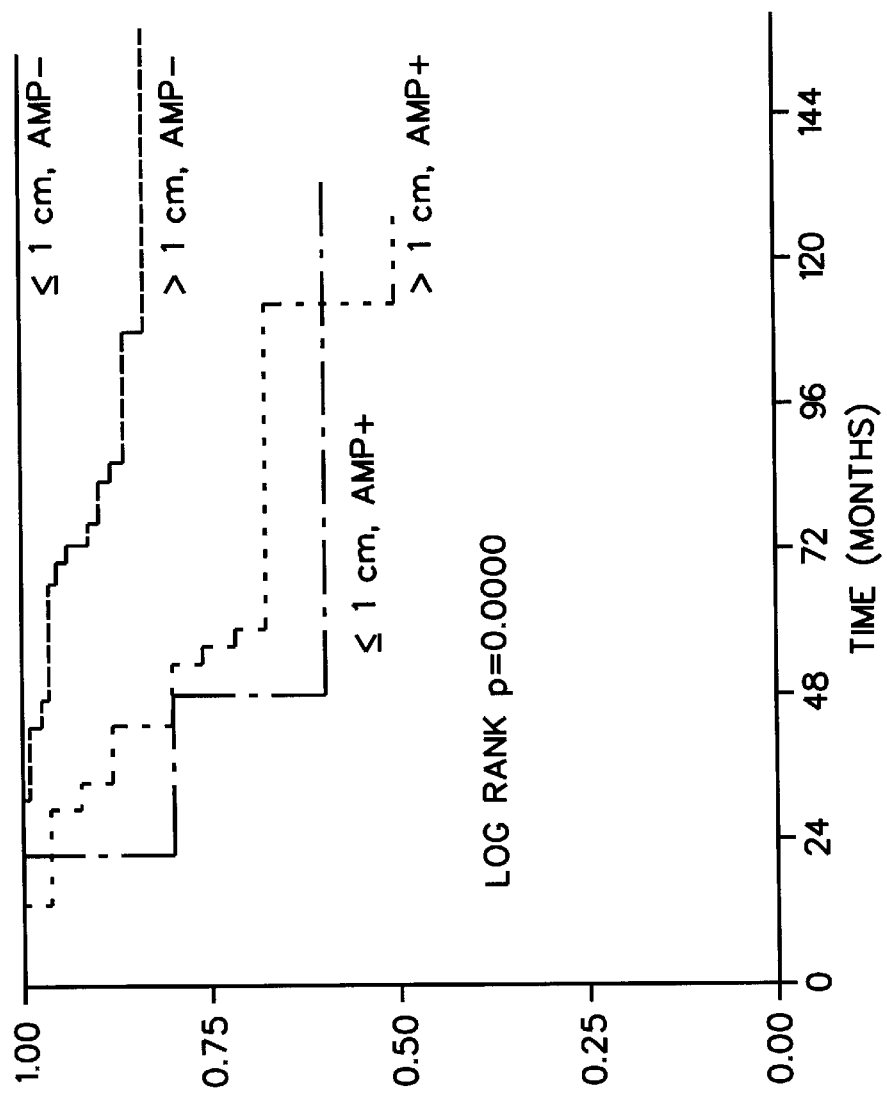
FIG. 2 an interaction, without error bars, of Her-2/neu amplification and tumor size cumulative probability of overall survival Her-2/neu Amplification Status (amp+/amp−) and tumor size (>1 cm/ <1 cm)

The survival curves presented in the figures are graphical representations of the probability of early recurrence-free survival, i.e., no recurrence within 24 months FIG. 1) survival for subjects with and without HER-2/neu amplification (FIG. 2). Error bars, where present, show the standard error around the values.

TABLE 4

Probability of disease-free survival of breast cancer patients with non-amplified and amplified lesions.

| Time from Surgery (in Years) | Probability of Remaining Disease-Free* | | | |
|---|---|---|---|---|
| | Non-Amplified | | Amplified | |
| | (95% CI)† | N** | (95% CI)† | N** |
| 0.5 | 100% (100.0% to 100.0%) | 179 | 93.8% (85.7% to 100.0%) | 31 |
| 1.0 | 98.3% (96.4% to 100.0%) | 176 | 81.8% (68.7% to 95.0%) | 27 |
| 1.5 | 96.7% (94.1% to 99.2%) | 173 | 75.8% (61.1% to 90.5%) | 25 |
| 2.0 | 94.4% (91.1% to 97.7%) | 169 | 75.8% (61.1% to 90.5%) | 25 |
| 2.5 | 93.9% (90.3% to 97.4%) | 168 | 72.7% (57.4% to 88.0%) | 24 |
| 3.0 | 93.3% (89.6% to 97.0%) | 167 | 69.7% (54.0% to 85.4%) | 23 |
| 5.0 | 85.9% (80.6% to 91.2%) | 121 | 66.7% (50.6% to 82.7%) | 19 |
| 10.0 | 70.5% (60.3% to 80.7%) | 23 | 61.9% (44.5% to 79.3%) | 4 |

Expansion of Table 4

Non-Amplified

| Time from Surgery (in years) | N** | Cumulative No. Events | Cumulative No. Cases Censored | Probability of Remaining Disease Free |
|---|---|---|---|---|
| 0.5 | 179 | 0 | 0 | 100.0% |
| 1.0 | 176 | 3 | 0 | 98.3% |
| 1.5 | 173 | 6 | 0 | 96.7% |
| 2.0 | 169 | 10 | 0 | 94.4% |
| 2.5 | 168 | 11 | 0 | 93.9% |
| 3.0 | 167 | 12 | 0 | 93.3% |
| 5.0 | 121 | 24 | 34 | 85.9% |
| 10.0 | 23 | 35 | 121 | 70.5% |

Amplified

| Time from Surgery (in years) | N** | Cumulative No. Events | Cumulative No. Cases Censored | Probability of Remaining Disease Free |
|---|---|---|---|---|
| 0.5 | 31 | 2 | 0 | 93.9% |
| 1.0 | 27 | 6 | 0 | 81.8% |
| 1.5 | 25 | 8 | 0 | 75.8% |
| 2.0 | 25 | 8 | 0 | 75.8% |
| 2.5 | 24 | 9 | 0 | 72.7% |
| 3.0 | 23 | 10 | 0 | 69.7% |
| 5.0 | 19 | 11 | 3 | 66.7% |
| 10.0 | 4 | 12 | 17 | 61.9% |

*Point estimate generated from the Kaplan Meier Statistic (Kaplan, E. L., and Meier, P., 1958)
†95% Confidence Interval (C.I.) generated from the Greenwood estimate of standard error (Greenwood, M., 1926)
**Number of Cases = number of cases at risk remaining in analyses at the time interval specified. The N values decrease with time due to patients experiencing an event (death or recurrence) or being censored (lost to follow-up).

TABLE 5

Probability of Overall Survival Tumor Size large (>1 cm)/small (<1 cm) and HER-2/neu Amplification Status Probability of overall survival of breast cancer patients with large/small and non-amplified/amplified tumors.

| Time from Surgery (in Years) | Probability of Survival* | | | |
|---|---|---|---|---|
| | Small (≦1 cm); Non-Amplified (≦4) | | Small (≦1 cm); Amplified (>4) | |
| | (95% CI)† | N** | (95% CI)† | N** |
| 0.5 | 100% (100.0% to 100.0%) | 39 | 100% (100.0% to 100.0%) | 5 |
| 1.0 | 100% (100.0% to 100.0%) | 39 | 100% (100.0% to 100.0%) | 5 |
| 1.5 | 100% (100.0% to 100.0%) | 39 | 100% (100.0% to 100.0%) | 5 |
| 2.0 | 100% (100.0% to 100.0%) | 39 | 80.0% (44.9% to 100.0%) | 4 |
| 2.5 | 100% (100.0% to 100.0%) | 39 | 80.0% (44.9% to 100.0%) | 4 |
| 3.0 | 100% (100.0% to 100.0%) | 39 | 80.0% (44.9% to 100.0%) | 4 |

TABLE 5-continued

Probability of Overall Survival Tumor Size large (>1 cm)/small (<1 cm) and HER-2/neu Amplification Status

| | | | | |
|---|---|---|---|---|
| 5.0 | 100% (100.0% to 100.0%) | 29 | 60.0% (17.1% to 100.0%) | 2 |
| 10.0 | 100% (100.0% to 100.0%) | 6 | 60.0% (17.1% to 100.0%) | 1 |

Probability of Survival*

| Time from Surgery (in Years) | Large (>1 cm), Non-Amplified ($\leq 4$) | | Large (>1 cm); Amplified (>4) | |
|---|---|---|---|---|
| | (95% CI)† | N** | (95% CI)† | |
| 0.5 | 100% (100.0% to 100.0%) | 117 | 100%(100.0% to 100.0%) | 25 |
| 1.0 | 100% (100.0% to 100.0%) | 117 | 100% (100.0% to 100.0%) | 25 |
| 1.5 | 100% (100.0% to 100.0%) | 117 | 96.0% (88.4% to 100.0%) | 24 |
| 2.0 | 100% (100.0% to 100.0%) | 117 | 96.0% (88.4% to 100.0%) | 24 |
| 2.5 | 99.2% (97.4% to 100.0%) | 116 | 96.0% (88.4% to 100.0%) | 24 |
| 3.0 | 99.2% (97.4% to 100.0%) | 116 | 88.0% (75.3% to 100.0%) | 22 |
| 5.0 | 96.4% (92.9% to 99.9%) | 89 | 68.0% (49.8% to 86.2%) | 15 |
| 10.0 | 83.4% (74.2% to 92.6%) | 21 | 51.0% (19.1% to 82.9%) | 3 |

*Point estimate generated from the Kaplan Meier Statistic (Kaplan, E. L., and Meier, P., 1958).
†95% Confidence Interval (C.I.) generated from the Greenwood estimate of standard error (Greenwood, M., 1926)
**Number of Cases = number of cases at risk remaining in analyses at the time interval specified.
Tumor size was available for 186 specimens out of the 210 specimens in the "disease-related death" database.
The table above is calculated from these 186 specimens.
The N values decrease with time due to patients experiencing an event (death or recurrence) or being lost to follow-up.

EXAMPLE VI

MULTI-TIERED CUTOFFS FOR HER-2/NEU GENE COPY

The data from the above testing was analyzed to determine the effect for using a $\leq 3$ cutoff and a $\leq 10$ cutoff on early recurrence (within 24 months), recurrence anytime and disease related death at any time. The relative hazard for each was calculated both unadjusted and adjusted for estrogen receptor, tumor size, patient age, study site and tumor grade. The results are in Tables 6.

TABLE 6

| | Relative Risk | | | | | |
|---|---|---|---|---|---|---|
| | Unadjusted | | | Adjusted | | |
| | $\leq 3$ cutoff | $\leq 10$ cutoff | $\geq 10$ | $\leq 3$ cutoff | $\leq 10$ cutoff | $\geq 10$ |
| Early Recurrence | 4.8 | 6.6 | 7.8 | 4.3 | 5.5 | 8.3 |
| Recurrence | 2.0 | 3.4 | 3.4 | 2.0 | 3.8 | 4.3 |
| Death | 4.7 | 5.8 | 6.9 | 4.5 | 7.3 | 11.0 |

As can be seen from this data, the higher the average HER-2/neu gene copy number per cell, the greater the risk to the patient.

Although preferred embodiments are specifically described herein, it will be appreciated that many modifications and variations of the present invention are possible in light of the above teachings and within the purview of the appended claims without departing from the spirit and intended scope of the invention. Other and further embodiments will be apparent to those in the art from the preceding description and examples. No unreasonable limitations or the like are to be drawn therefrom in interpreting the following claims.

References cited in text and related to the invention.
American Cancer Society (ACS), 1997. Cancer facts and figures; Atlanta Ga.: The American Cancer Society.
Clinical Oncology: *A Multidisiplinary Approach for Physicians and Students*, 7th Edition. Editor P. Rubin, M. D.), W. B. Saunders Company, Philadelphia, Pa., 1993, pg. 207.
Cox, D. R, 1972. Regression models and life-tables (with discussion); *Journal of the Royal Statistical Society*, B, 34: 187–220.
Glick, J., 1988. Meeting highlights: Adjuvant therapy for breast cancer; *Journal of the National Cancer Institute*, 80:471–475.
Greenwood, M., 1926. The natural duration of cancer. *Reports on Public Health and Medical Subjects*, Vol. 3, Her Maesty's Stationazy Office, London: I-26.
Human Gene Mapping 11, 1991. London Conference (1991) Eleventh International Workshop on Human Gene Mapping; *Cytogenetics and Cell Genetics, Solomon*, E., Rawlings, C., eds., Karger, 58:1–4:702.
Iglehart, J. D., Kraus, M. H, Langton, B. C., Huper, G., Kems, B. J., Marks, J. R., 1990. Increased erbB-2 gene copies and expression in multiple stages of breast cancer; *Cancer Res.*, 50:6701–6707.
Kaplan, E. L., & Meier, P. L., 1958: Non-parametric Estimation from Incomplete Observations; *Journal of the American Statistical Association*, 53:447–491.
Kallioniemi, O. P., Kallioniemi, A., Kurisu, W., Thor, A., Chen, L. C., Smith, H S., Waldman, F. M., Pinkel, D., Gray, J. W., 1992. ERBB2 amplification in breast cancer analyzed by fluorescence in situ hybridization; *Proc. Nati. Acad Sci. USA*, 89:12:5321–5325.
McGuire, W., Tandon, A., Allred, C., Chamnes, G., Clark, G., 1990. How to use prognostic factors in axiblazy node-negative breast cancer patients; *J. Natl. Cancer Inst.*, 82:12:1006–1015.
National Cancer Institute (NCI), Clinical Alert from the National Cancer Institute, Department of Health and Human Services, Bethesda, Md., May 16, 1988.

Niehans, G. A., Singleton, T. P., Dykoskd, D., Kiang, D. T., 1993. Stability of HER-2/neu expression over time and at multiple metastatic sites; *J. Natl Cancer Inst*, 85:15:1230–1235.

Press, M. F., Hung, G., Godolphin W., Slamon, D. J., 1994. Sensitivity of HER-2/neu antibodies in archival tissue samples: Evaluation of immunostaining in multi-tumor tissue blocks of breast cancers with molecularly characterized application and expression levels; *Cancer Res.*, 54:2771–2777.

Ro, J., El-Naggar, A., Ro, J., et al., 1989. c-erbB-2 amplification in node negative human breast cancer; *Cancer Research*, 49:6941.

Seshadri, R., Firgaria, F. A., Horsfall, D. J., McCaul, K., Setlur, V., Kitchen, P., 1993. Clinical significance of HER-2/neu oncogene amplification in primary breast cancer; *Journal of Clin. Oncology*, 11:10:1936–1942.

Tsuda, H., Hirohashi, S., Shimosato, Y., Hirota, T., Tsugane, S., Yamamoto, H., Miyajima, N., Toyoshima, K., Yamamoto, T., Yokota, J., Yoshida, T., Sakamoto, H., Terada, M., Sugimura, T., 1989. Correlation between long-term survival in breast cancer patients and amplification of two putative oncogene coamipilfication units; hst-1/int-2 and c-erbB-2/ear-1; *Cancer. Res.*, 49:3104–3108.

Van de Vijver, M. J., Peterse, J. L., Mooi W. J., et al, 1988. Neu-Protein overexpression in breast cancer. Association with comedo-type ductal carcinoma in situ and limited prognostic value in stage II breast cancer, *N. Engl. J. Med.*, 319:1239–1245.

Wright, C., Nicholson, S., et al., 1989. Expression of c-erbB-2 oncoprotein: a prognostic indicator in human breast cancer; *Cancer Research*, 49:2087.

Zweig, M. H., and Campbell, G., 1993. Receiver-Operating Characteristic (ROC) Plots: A Fundamental Evaluation Tool in Clinical Medicine; *Clinical Chemistry*, 39:561–577.

OTHER REFERENCES RELATED TO SUBJECT MATTER

Ali, I., Campbell, G., Lidereau, R., Callahan, R., 1988. Amplification of c-erbB-2 and aggressive human breast tumors; *Science*, 240:1795–1798.

Allred, D. C., Clark, G. M., Tandon, A. K., Molina, R., Torney, D. C., Osborne, C. K., Gilchrist, K. W., Mansour, E. G., Abeloff, M., Eudey, L., McGuire, W. L., 1992a. HER-2/neu in node-negative breast cancer prognostic significance of overexpression influenced by the presence of in situ carcinoma; *Journ. of Clin Oncology*, 10:4:599–605.

Allred, D. C., Clark, G. M., Molina, R., Tandon, A., Schnitt, S. J., Gilchrist, K. W., Osborne, C. K., Tormey, D. C., McGuire, W. L., 1992b. Overexpression of HER-2/neu and its relationship with other prognostic factors change during the progression of in situ to invasive breast cancer; *Human Pathology*, 23:9:974–979.

Bacus, S. S., Ruby, S. G., Weinberg, D. S., Chin, D., Ortiz, R., Bacus, J. W., 1990. HER-2/neu oncogene expression and proliferation in breast cancers; *Amer Journal of Pathol.*, 137:1:103–111.

Battifora, H., Gaffey, M., Esteban, J., Mehta, P., Bailey, A., Faucett, C., Niland, J., 1991. Immunohistochemical assay of neulc-erbB-2 oncogene product in paraffin-embedded tissues in early breast cancer: retrospective follow-up study of 245 stage I and II cases, *Modern Pathology*, 4:4:466–474.

Baum, M., Brinkley, D., Dosset, J., 1988. Controlled trial of tamoxifen as a single adjuvant agent in the management of early breast cancer. Analysis at eight years by Nolvadex Adjuvant Trial Organization; *British Journal of Cancer*, 57:608–611.

Berns, E. M. J. J., Klijn, J. G. N., Van Staveren, I. L., Portengen, H., Noordegraaf E., Foedens, J. A., 1992. Prevalence of amplification of the oncogenes c-myc, HER2/neu, and int-2 in one thousand human breast tumors: Correlation with steroid receptors; *Eur. J. Cancer*, 28: 697–700.

Borg, A, Tandon, A. K., Sigurdsson, I., Clark, G. M., Fernó, M., Fuqua, S. A. W., Killander, D., McGuire, W. L., 1990. HER-2/neu amplification predicts poor survival in node-positive breast cancer; *Cancer Research*, 50:4332–4337.

Borg, A., Baldetorp, B., Fernó, M., Killander, D., Olsson, H., Sigurdsson, H., 1991a. ERBB2 amplification in breast cancer with a high rate of proliferation; *Oncogene*, 6:137–143.

Borg, A., Sigurdsson, H., Clark, G. M., Fernó, M., Fuqua, S. A. W., Olsson, H., Killander, D., McGurie, W. L., 1991b. Association of INT2/HST1 coamplification in primary breast cancer with hormone-dependent phenotype and poor prognosis; *Br. Jounal Cancer*, 63:1:136–142.

Bouchard, L., Lamarre, L., Tremblay, P. J., Jolicoeur, P., 1989. Stochastic appearance of mammary tumors in transgenic mice canying the MMTV/c-neu oncogene; *Cell*, 57:931–936.

Breast Cancer Trials Committee, Scottish Cancer Trials Office, Edinburgh, 1987. Adjuvant tamoxifen in the management of operable breast cancer: The Scottish Trial. *Lancet*, 2, 171–175.

Callahan, R., Campbell, G., 1989. Mutations in human breast cancer: an overview; *J. Natl. Cancer Inst.*, 81:1780–1786.

Clark, G. M., McGuire, W. L., 1991. Follow-up study of HER-2/neu amplification in primary breast cancer, *Cancer Res*, 51:944–948.

Coussens, L., Yang-Feng, T. L., Liao, Y. C., Chen, E., Gray, A., Mcrath, J., Seeburg, P. H., Libermann, T. A., Schliessinger, J., Francke, U., Levinson A., Ullrich, A., 1985. Tyrosine kinase receptor with extensive homology to EGF receptor shares chromosomal location with neu oncogene; *Science*, 230:1132–1139.

Descotes, F., Pavy, J. J., Adessi G. L., 1993. Human breast cancer correlation study between HER-2/neu amplification and prognostic factors in an unselected population; *Anticancer Research.*, 13:1:119–124.

Donovan-Peluso, M., Contento, A. M., Tobon, H., Ripepi, B., Locker, J., 1991. Oncogene amplification in breast cancer; *Amer. Journal of Pathology*, 138:4:835–845.

Drebin, J. A., Link, V. C., Weinberg, R. A., Greene, Mich., 1986. Inhibition of tumor growth by a monoclonal antibody reactive with an oncogene-encoded tumor antigene; *PNAS USA*, 83:9129–9133.

Dressier, L. G., Seamer, L. C., Owens, M. A., Clark, G. M., McGuire, W. L., 1988. DNA flow cytometry and prognostic factors in 1331 frozen breast cancer specimens; *Cancer*, 61:420–427.

Fallenius, A. G., Auer, G. U., Carstensen, J. M., 1988. Prognostic significance of DNA measurements in 409 consecutive breast cancer patients; *Cancer*, 62:331–341.

Fisher, B., Constantino, J., Redmond, C., 1989a A randomized clinical trial evaluating tamoxifen in the treatment of patients with node-negative breast cancer who have estrogen-receptor-positive tumors; *New England Journal of Medicine*, 320:479–484.

Fisher, B., Redmond, C., Nikolay, V., 1989b. A randomized clinical trial evaluating sequential methotrexate and fluorouracil in the treatment of patients with node-negative breast cancer who have estrogen-receptor-negative tumors; *New England Journal of Medicine*, 320:473–478.

Fisher, E. R., Redmond, C., Fisher, B., Bass, G., BSS and contributing NSABP Investigators, 1990. Pathologic findings from the national surgical adjuvant breast and bowel projects NSABP); *Cancer*, 65:2121–2128.

Fontaine, J., Tesseraux, M., Klein, V., Basieri, G., Blin, N., 1988. Gene amplification and expression of the neu (c-erbB-2) sequence in human mammar carcinoma; *Oncology* (15) 45:360–363.

Fukushige, S. I., Matsubara, K. I., Yoshida, M., et al., 1986Localization of a novel v-erbB-related gene, c-erbB-2, on human chromosome 17 and its amplification in a gastric cancer cell line, *MoL Cell Biol.*, 6:955–958.

Giampietro, G., Gullick, W. J., Bevilacqua, P., Sainsbury, R. C., Meli, S., Boracchi, P., Testolin, A., La Malfa, G., Pozza, F., 1992. Human Breast Cancer: Prognostic significance of the c-erbB-2 oncoprotein compared with epidermal growth factor receptor, DNA Ploidy, and conventional pathologic features; *Journal of Clinical Oncol*, 10:686–695.

Gullick, W. J., Love, S. B., Wright, C., Barnes, D. M., Gusterson, B., Harris, A. L., Altman, D. G., 1991. cerbB-2 protein overexpression in breast cancer is a risk factor in patients with involved and uninvolved lymph nodes, *Br. Journal of Cancer*, 63:434–438.

Gusterson, B. A., Gelber, R. D., Goldhirsch, A., Price, K. N., Save-Soderbergh, J., Anbazhagan, R., Styles, J., Rudenstam, C. M., Golouh, R., Reed, R., Marinez-Tello, F., Tiltman, A., Torhorst, J., Grigolato, P., Beitelheim, R., Neville, A. M., Burki, K., Castiglione, M., Collins, J., Lindtner, J., Senn, H-J., for the International Ludwig Breast Cancer Study Group, 1992. Prognostic Importance of c-erbB-2 expression in breast cancer; *Journal of Clinical Oncol*, 10: 1049–1056.

Harris, J. R., Lippman, M. E., Veronesi U., Willett, W, 1992. Breast Cancer; *The New England Journal of Medicine*, 6:390–398.

Hillner, B. E., Smith, T. J., 1991. Efficacy and cost effectiveness of adjuvant chemotherapy in women with node-negative breast cancer, *New. England Journal of Medicine*, 324:160–168.

Isola, J., Visakorpi T., Holli K., Kallioniemi, O., 1992. Association of overexpression of tumor suppressor protein p53 with rapid cell proliferation and poor prognosis in node-negative breast cancer patients; *Journal National Cancer Inst.*, 84:14:1119–1114.

Kallioniemi, O. P., Holli, K., Visakorpi, T., Helin, H. H., Isola, J. J., 1991. Association of c-erB-2 protein overexpression with high rate of cell proliferation, increased risk of visceral metastasis and poor long-term survival in breast cancer, *Int Journal Cancer*, 49:5: 650–655.

King, C. R., Kraus, M. H., Aaronson, S. A., 1985. Amplification of a novel v-erbB-related gene in a human mammary carcinoma; *Science*, 229:974–976.

Kraus, M. H., Popescu, N. C., Amsbaugh, S. C., King C. R., 1987. Overexpression of EGF Receptor-related proto-oncogene erbB-2 in human mammary tumor cell lines by different molecular mechanisms; *EMBO Journal*, 6:605–610.

Kury, F., Sliutz, G., Schemper, M., Reiner, G., Reiner, A., Jakesz, R., Wrba, F., Zeillinger, R., Knogler, W., Huber, J., Holzner, H., Spona, J., 1990. HER-2 oncogene amplification and overall survival of breast carcinoma patients; *European Journal of Cancer*, 26:9:946–949.

Liu, E., Thor, A., He, M., Barcos, M., Ljung, B. M., Benz C., 1992. The HER-2 (cebB-2) oncogene is frequently amplified in situ carcinomas of the breast; *Oncogene*, 7:5:1027–32.

Lovekin, C., Ellis, I. O., Locker, A., Robertson, J. F. R., Bell J., Nicholson, R., Gullick, W. J., Elston, C. W., Blamey, R. W., 1991. c-erbB-2 oncoprotein expression in primary and advanced breast cancer; *British Journal of Cancer*, 63:439–443.

Maguire, H. C., Heilum, M. E., Greene, M. I., Yeh, I., 1992. Expression of c-erbB-2 in situ and in adjacent invasive ductal adenocarcinomas of the female breast; *Pathobiology*, 60:3:117–121.

Maikin, D., Li, F. P., Strong, L. C., Fraumeni, Jr., J. F., Nelson, C. E., Kim, D. H., Kassel, J., Gryka, M. A., BischofF. Z., Tainsky, M. A., Friend, S. H., 1990. Germ line p53 mutations in a familial syndrome of breast cancer, sarcomas, and other neoplasms, *Science*, 250:1233–1238.

Mansour, E., Gray, R., Shatila, A., 1989. Efficacy of adjuvant chemotherapy in high risk node-negative breast cancer, *New England Journal of Medicine*, 320:485490.

McCann, A. H., Dervan, P. A., O'Regan, M., Codd, M. B., Gullick, W. J., Tobin, B. M., Carney, D. N., 1991. Prognostic significance of c-erbB-2 and estrogen receptor status in human breast cancer, *Cancer Res.*, 51:3296–3303.

McGuire, W., 1989a. Adjuvant therapy of node-negative breast cancer, *New Englad Journal of Medicine.*, 320:525–527.

McGuire, W., 1989b. Adjuvant therapy of node-negative breast cancer: another point of view; *Journal of the National Cancer institute*, 80:1075–1076.

McGuire, W. L., Clark, G., 1992. Prognostic factors and treatment decisions in axillary-node-negative breast cancer; *New England Journal of Medicine*, 326:26:1756–1761.

Molina, R., Ciocca, D. R., Tandon, A. K., Allred, D. C., Clark, G. M., Chamness, G. C., Gullick, W. J., McGuire, W. L., 1992. Expression of HER-2/neu oncoprotein in human breast cancer: a comparison of immunohistochemical and western blot techniques; *Anticancer Research.*, 12:1965–1972.

Muller, W. J., Sinn, E., Pattengale, P. K., et al., 1988. Single-step induction of mammary adenocarcinoma in transgenic mice bearing the activated c-neu oncogene; *Cell*, 54:105–111.

Neville, A. M., 1991. Detection of tumor antigens with monoclonal antibodies: immunopathology and immunodiagnosis, *Curr Opin. Immunol.*, 3:674–678.

NIH Consensus Development Panel. Consensus statement treatment of early-stage breast cancer In: Consensus development conference on the treatment of early-stage breast cancer. *Journal of the National Cancer Institute monographs*, No. 11., Washington, D.C., Government Printing Office, 1–5, 1992 (NIH publication no. 903187).

O'Reilly, S. M., Barnes, D. M., Camplejohn, R. S., Bartkova, J., Gregory, W. M., Richards, M. A., 1991. The relationship between c-erbB-2 expression, S-phase fraction and prognosis in breast cancer; *Br. J. Cancer*, 63:3:444–446.

Page, D. L., 1991. Prognosis and breast cancer; *The American Journal of Surgical Path.*, 15:4:334–349.

Paik, S., Hazan, R., Fisher, E., Sass, R. E., Fisher, B., Redmon, C., Schlessinger, J., Lippman, M. E., King, C. R., 1990. Pathological findings from the National Surgical Adjuvant Breast and Bowel Project: prognostic significance of erbB2 protein overexpression in primary breast cancer; *Journal of Clinical Oncology*, 8:103–112.

Patterson, M. C., Dietrich, K. D., Danyluk, J., Paterson, A. H. G., Lees, A. W., Jamil, N., Hanson, J., Jenkins, H., Krause, B. E., McBLain, W. A., Slamon, D. J., Fourney, R. M., 1991. Correlation between c-erbB-2 amplification and risk of recurrent disease in node-negative breast cancer; *Cancer Research*, 51 :556–567.

Pauletti, G., Godolphin, W., Press, M. F., Slamon, D. J. 1996. Detection and quantitation of HER-2/neu gene amplification in human breast cancer archival material using fluorescence in situ hybridization; *Oncogene*, July 4;13(1): 63–72.

Perren, T. J., 1991. cerbB-2 oncogene as a prognostic marker in breast cancer; *British Journal of Cancer*; 63:328–332.

Persons, D. L., Borelli, K. A., Hsu, P. H. 1997. Quantitation of HER-2/neu and c-myc gene amplification in breast carcinoma using fluorescence in situ hybridization; *Mod Pathol*,July; 10(7):720–727.

Press, M. F., Bernstein, L, Thomas, P. A., Meisner, L. F., Zhou, J. Y., Ma, Y., Hung, G., Robinson, R. A., Harris, C., El-Naggar, A., Slamon, D. J., Phillips, R. N., Ross, J. S., Wolman, S. R., Flom, K. J., 1997. HER-2/neu gene amplification characterized by fluorescence in situ hybridization: poor prognosis in node-negative breast carcinomas; *Journal of Clinical Oncol*, Aug;15(8):2894–2904.

Press, M., Cordon-Carlo, C. and Slamon, D., 1990. Expression of the HER-2/neu protooncogene in normal adult and fetal tissues; *Oncogene*, 5: 953–962.

Press, M. F., Pike, M. C., Chazin, V. R., Hung G., Udove, J. A., Markowicz, M., Danyluk, J., Godolphin, W., Sliwkowski, M., Akita., R, Paterson, M. C., Slamon, D. J., 1993. HER-2/neu Expression in Node-negative Breast Cancer: Direct Tissue Quantitation by Computerized Image Analysis and Association of Overexpression with Increased Risk of Recurrent Disease; *Cancer Research*, 53:4960–4970.

Rhein R., 1993. Early study results of antibodies targeting HER-2 proteins seen as promising; *Cancer and Genetics Report*, pages 8–9.

Richner, J., Gerber, H. A., Locher, G. W, Goldhirsch, A., Gelber, R. D., Gullick, W. J., Berger, M. S., Groner, B., Hynes, N. E., 1990. c-erb B-2 protein expression in node negative breast cancer, *Annals Oncol.*, 1: 263–268.

Rilke, F., Colnaghi, M. L., Cascinelli, N., Andreola, S., Baldini, M. T., Bufalino, R., Porta, G. D., Menard, S., Pierotti, M. A., Testori, A., 1991. Prognostic significance of HER-2/neu expression in breast cancer and its relationship to other prognostic factors; *Int. J. Cancer,* 49:44–49.

Rodriguez, G. C., Boente, M. P., Berchuck, A, Whitaker, R. S., O'Briant, K. C., Xu, F., Bast, R. C., 1993. The effect of antibodies and immunotoxins reactive with HER-2/neu on growth of ovarian and breast cancer cell lines; *Am. J. Obstet Gynecol*, 168:1:1:228–232.

Rosai, J., 1991. Borderline epilhelial lesions of the breast; *Amer. J. Surg. Path.*, 15:209–221.

Ross, J. S., Nazeer, T., Church, K, Amato, C., Figge, H., Rifkin, M. D., Fisher, A. G., 1993. Contribution of HER-2/neu Oncogene Expression to Tumor Grade and DNA Content Analysis in the Prediction of Prostatic Carcinoma Metastasis; *Cancer*, 72:3020–3028.

Schimmelpenning H., Eriksson, E. T., Falkmer, U. G., Azavedo, E., Svane, G., Auer, G. U., 1992. Expression of the c-erbB-2 protooncogene product and nuclear DNA content in benign and malignant human breast parenchyma; *Virchows Arch. A Pathol. Anat Histopathol*, 420:5:433–440.

Singleton, T. P., Stickler, J. G., 1992. Clinical and pathologic significance of the c-erbB-2 (HER-2/neu) oncogene; *Pathol. Annu.*, 27:165–190.

Slamon, D. J., Clark, G. M., Wong, S. G., Levin, W. J., Ullrich, A., McGuire, W. L., 1987. Human breast cancer: correlaion of relapse and survival with amplification of the HER-2/neu oncogene; *Science*, Januray 9;235(4785): 177–182.

Slamon, D. J., Godolphin, W., Jones, L., Holt, J., Wong. S., Keith, D., Levin, W., Stuart, S., Udove, J., Ullrich and Press, M., 1989a Studies of ihe HER-2/neu proto-oncogene in human breast and ovarian cancer, *Science*, 244:707–712.

Slamon, D. J., Press, M. F., Godolphin, W., Ramos, L., Haran, P., Shek, L., St, S. G., Ullrich, A., 1989b. Studies of the HER-2/neu proto-oncogene in human breast cancer, *Cancer Cells*, 7:371–384.

Tandon, A. K., Clark, G. M., Chamess, G. C., et al., 1989. HER-2/neu oncogene protein and prognosis in breast cancer; *J. Clin. Oncol*, 7:1120–1128.

Thor, A. D., Schwartz, L. H., Koerner, F. C., et al., 1989 Analysis of c-erbB-2 expression in breast carcinomas with clinical follow-up; *Cancer Res.*, 49:7147–7152.

Tiwari, R., Borgen, P. I., Wong, G. Y., Cordon-cardo, C., Osborne, M. P., 1992. HER-2/neu amnplification and overexpression in primaly human breast cancer is associated with early metastasis; *Anticancer Research*, 12:419–426.

Tommasi, S., Giannella, C., Paradiso, A., Barletta, A., Mangia, A., Simone, G., Primavera, A. T., Albarani, V., Schittulli, F., Longo, S., 1992. HER-2/neu gene in primary and local metastatic auxiliary lymph nodes in human breast tumors; *Int. J. Biol. Markers*, 7:2:107–113.

Tsuda, H., Hirohashi, S., Shimosato, Y., Hirota, T., Tsugane, S., Watanabe, S., Terada, M., Yamamoto, H., 1990. Correlation between histologic grade of malignancy and copy number of c-erbB-2 gene in breast carcinoma A retrospective analysis of 176 cases; *Cancer*, 65:1794–1800.

Van de Vijver, M., van de Bersselaar, R., Devilee, P., et al., 1987. Amplification of the neu (c-erbB-2) oncogene in human mammary tumors is relatively frequent and is often accompanied by amplification of the liked c-erbA oncogene; *Mol. Cell Biol.*, 7:2019–2023.

Winstaley, J., Cooke, T., George, W. D., Murray, G., Holt, S., Croton, R, Griffiths, K., Nicholson, R., 1991. The long term prognostic significance of oestrogen receptor analysis in early carcinoma of the breast; *British J. Cancer*, 64:99–101.

Wolman, S. R., Henderson, A. S., 1989. Chromosomal aberrations as markers of oncogene amplification.; *Human Pathology*, 20:308–315.

Xing, W. R., Gilchrist, K. W., Harris, C. P., Samson, W., Meisner, L. F. 1996. FISH detection of HER-2/neu oncogene amplification in early onset breast cancer; *Breast Cancer Research Treat*;39(2):203–212.

Xu, F., Lupu, R., Rodriguez, G. C., Whitaker, R. S., Boente M. P., Berchuck, A., Yu, Y., Desombre, K. A., Boyer, C. M., Bast R. C., 1993. Antibody-induced growth inhibition is mediated through immunochemically and functionally distinct epitopes on the extracellular domain of the c-erbB-2 (HER-2/neu) gene product; *Int. J. Cancer*, 53:3:401–408.

Zhou, D., Ahuja, H. and Cline, M., 1989. Proto-oncogene abnormalities in human breast cancer: c-ERB-2 amplification does not correlate with recurrence of disease; *Oncogene*, 4:105–108.

All references mentioned above are herein incorporated by reference.

We claim:

1. A method for determining the likelihood of cancer recurrence in a patient comprising the steps of:
   (a) obtaining tumor cells from the patient; (b) applying to each of said cells a detectable probe capable of hybridizing to the HER-2/neu gene;
   (c) counting the number of HER-2/neu genes per cell; and
   (d) determining the likelihood of cancer recurrence wherein an average of about 10 or more HER-2/neu genes per tumor cell indicates a high likelihood of cancer recurrence and an average of about 3 or fewer HER-2/neu genes per tumor cell indicates a low likelihood of cancer recurrence.

2. The method according to claim 1 wherein a control cell line is substantially simultaneously tested.

3. The method according to claim 1 wherein the number of cells counted is about 40.

4. The method according to claim 1 wherein the number of cells counted is about 20.

5. A method for determining the likelihood of cancer recurrence in a patient comprising the steps of:
   (I) obtaining tumor cells from the patient;
   (ii) applying to said cells a detectable probe capable of hybridizing to the HER-2/neu gene;
   (iii) counting the number of HER-2/neu genes in cells; and
   (iv) determining the likelihood of cancer recurrence wherein an average of at least about 4 HER-2/neu genes per tumor cell indicates a high likelihood of cancer recurrence.

6. The method according to claim 5 wherein at least one control cell line is substantially simultaneously tested.

7. The method according to claim 5 wherein the number of cells with HER-2/neu genes counted therein is no more than about 20.

8. A kit of quality control cell lines for a HER-2/neu gene amplification detection system comprising:
   (i) a non-amplified control cell line that exhibits a mean of about 3 or fewer HER-2/neu genes per cell; and
   (ii) an amplified control cell line that exhibits a mean of about 10 or more HER-2/neu genes per cell.

9. The kit according to claim 8 and further comprising a low amplified control cell line that exhibits a mean of between about 3 and 10 HER-2/neu genes per cell.

10. A kit of quality control cell lines for use with a breast cancer gene amplification detection system according to claim 9 comprising:

(I) ATCC HTB 30 (SK-BR-3) cell line;
(ii) ATCC HTB 132 (MDA-MB468) cell line; and
(iii) ATCC HTB 133 (T-47D) cell line.

11. A kit for determining the number of copies of HER-2/neu genes in a cell comprising;
   a) a detectable probe capable of hybridizing to the HER-2/neu gene; and
   b) at least one control cell line selected from the group consisting of one that exhibits a mean of about 10 or more HER-2/neu genes per cell, one that exhibits a mean of between about 3 and 10 HER-2/neu genes per cell, and one that exhibits a mean of about 3 or fewer HER-2/neu genes per cell.

12. The kit according to claim 11 further comprising at least two of the control cell lines.

13. The kit according to claim 12 further comprising all three of the control cell lines.

14. A quality control material for use as a standardized control comprising:
   (a) a first cell line having an amplified HER-2/neu gene copy number, and
   (b) a second cell line having a non-amplified HER-2/neu copy number; wherein all of the cells in the quality control material are distributed throughout a solid medium in three dimensions.

15. A thin section of a quality control material consisting essentially of a thin section cut from the material of claim 14.

16. A method for determining the likelihood of cancer recurrence in a patient comprising the steps of:
   (a) obtaining tumor cells from the patient;
   (b) measuring the level of amplification of the HER-2/neu gene in said cells using fluorescence in situ hybridization;
   (c) determining the likelihood of cancer recurrence wherein an average of about 10 or more HER-2/neu genes per tumor cell indicates a high likelihood of cancer recurrence and an average of about 3 or fewer HER-2/neu genes per tumor cell indicates a low likelihood of cancer recurrence.

* * * * *